United States Patent [19]
Fischer

[11] Patent Number: 5,246,371
[45] Date of Patent: Sep. 21, 1993

[54] METHOD AND APPARATUS FOR DELIVERY OF HIGHLY FILLED, THIXOTROPIC SEALANT TO TEETH

[75] Inventor: Dan E. Fischer, Sandy, Utah

[73] Assignee: Ultradent Products, Inc., South Jordan, Utah

[21] Appl. No.: 939,082

[22] Filed: Sep. 1, 1992

Related U.S. Application Data

[63] Continuation-in-part of Ser. No. 940,204, Aug. 31, 1992.

[51] Int. Cl.⁵ .......................... A61C 5/00; A61C 5/04
[52] U.S. Cl. ................................ 433/217.1; 433/226; 433/90
[58] Field of Search ................ 433/89, 90, 217.1, 226; 401/129, 196; 604/2, 310, 311

[56] References Cited

U.S. PATENT DOCUMENTS

| | | | |
|---|---|---|---|
| 374,026 | 11/1987 | Williams . | |
| 392,006 | 10/1988 | Carmichael . | |
| 762,603 | 6/1904 | Witkowski . | |
| 833,044 | 10/1906 | Goodhugh . | |
| 860,555 | 7/1907 | Middaugh . | |
| 977,825 | 1/1910 | Murphy . | |
| 1,115,561 | 11/1914 | Northey . | |
| 1,164,430 | 12/1915 | Thurman . | |
| 1,245,153 | 11/1917 | Evslin . | |
| 1,438,064 | 12/1922 | Simmons . | |
| 1,573,224 | 2/1926 | Condit . | |
| 1,711,352 | 4/1929 | Jeffreys . | |
| 1,711,516 | 5/1929 | Alland . | |
| 1,908,403 | 5/1933 | Budde . | |
| 2,090,354 | 8/1937 | Massman . | |
| 2,100,157 | 11/1937 | Chandler | 128/269 |
| 2,104,651 | 1/1938 | Hoffman | 132/73 |
| 2,643,655 | 6/1953 | McKay | 128/220 |
| 2,754,590 | 7/1956 | Cohen . | |
| 3,175,242 | 3/1965 | Kamondy | 15/559 |
| 3,234,918 | 2/1966 | Gigli | 120/45.4 |
| 3,270,743 | 9/1966 | Gingras | 128/215 |
| 3,337,095 | 8/1967 | Marbach et al. | 222/309 |
| 3,346,147 | 10/1967 | Higgins et al. | 222/326 |
| 3,369,543 | 2/1968 | Ronco | 128/269 |
| 3,434,209 | 3/1969 | Weissman | 33/15 |
| 3,462,840 | 8/1969 | Ellman | 32/60 |
| 3,512,526 | 5/1970 | Fielding | 128/239 |
| 3,519,364 | 7/1970 | Truhan | 401/177 |
| 3,572,337 | 3/1971 | Schunk | 128/222 |
| 3,581,399 | 6/1971 | Dragan | 32/60 |

(List continued on next page.)

Primary Examiner—John J. Wilson
Assistant Examiner—Nicholas D. Lucchesi
Attorney, Agent, or Firm—Workman Nydegger Jensen

[57] ABSTRACT

A method and apparatus for delivery of highly filled, thixotropic resin sealant to tooth surfaces. The apparatus includes a dispenser for holding a quantity of the sealant material and a delivery tip having adjustable bristles at one end. The bristles are slidably secured in a spiral passageway formed by a helical ridge inside the delivery tip, thereby allowing the sealant material to be continuously applied without the need to stop the procedure and rewet the applicator. The applicator permits accurate control of the amount of sealant material applied to the surface. In this way, the surface receives neither an excessive nor an insufficient amount of the sealant material. Moreover, the bristles may be pushed in to permit the sealant material to be applied to a small, irregular surface, such as pits and fissures, or pulled out to permit the bristles to fan out for application to broad surface areas. Delivery of highly filled, relatively viscous, thixotropic sealant materials is made possible by providing the spiral passageway around the bristles so that the coating material does not have to flow through the bristles, and due to sheer thinning caused by forcing the thixotropic material through the spiral passageway.

7 Claims, 3 Drawing Sheets

U.S. PATENT DOCUMENTS

| | | | |
|---|---|---|---|
| 3,587,575 | 6/1971 | Lichtenstein | 128/215 |
| 3,759,259 | 9/1973 | Truhan | 128/269 |
| 3,760,503 | 9/1973 | Baskas | 128/218 |
| 3,792,699 | 2/1974 | Tobin et al. | 128/2 W |
| 3,894,538 | 7/1975 | Richter | 128/260 |
| 3,896,552 | 7/1975 | Russell | 32/34 |
| 3,902,035 | 9/1975 | Hartley | 128/234 |
| 3,910,706 | 10/1975 | Del Bon | 401/134 |
| 3,918,435 | 11/1975 | Beall et al. | 128/2 W |
| 3,924,623 | 12/1975 | Avery | 128/269 |
| 3,938,898 | 2/1976 | Reitknecht | 401/183 |
| 4,030,496 | 6/1977 | Stait et al. | 128/215 |
| 4,143,428 | 3/1979 | Cohen | 3/36 |
| 4,157,709 | 6/1979 | Schuster et al. | 128/759 |
| 4,225,254 | 9/1980 | Holberg et al. | 401/119 |
| 4,243,035 | 1/1981 | Barrett | 128/215 |
| 4,318,403 | 3/1982 | Sneider | 128/232 |
| 4,329,990 | 5/1982 | Sneider | 128/239 |
| 4,522,593 | 6/1985 | Fischer | 433/136 |
| 4,551,100 | 11/1985 | Fischer | 433/218 |
| 4,578,055 | 3/1986 | Fischer | 604/2 |
| 4,813,871 | 3/1989 | Friedman | 433/90 |
| 4,941,873 | 7/1990 | Fischer | 604/54 |
| 4,997,371 | 3/1991 | Fischer | 433/90 |

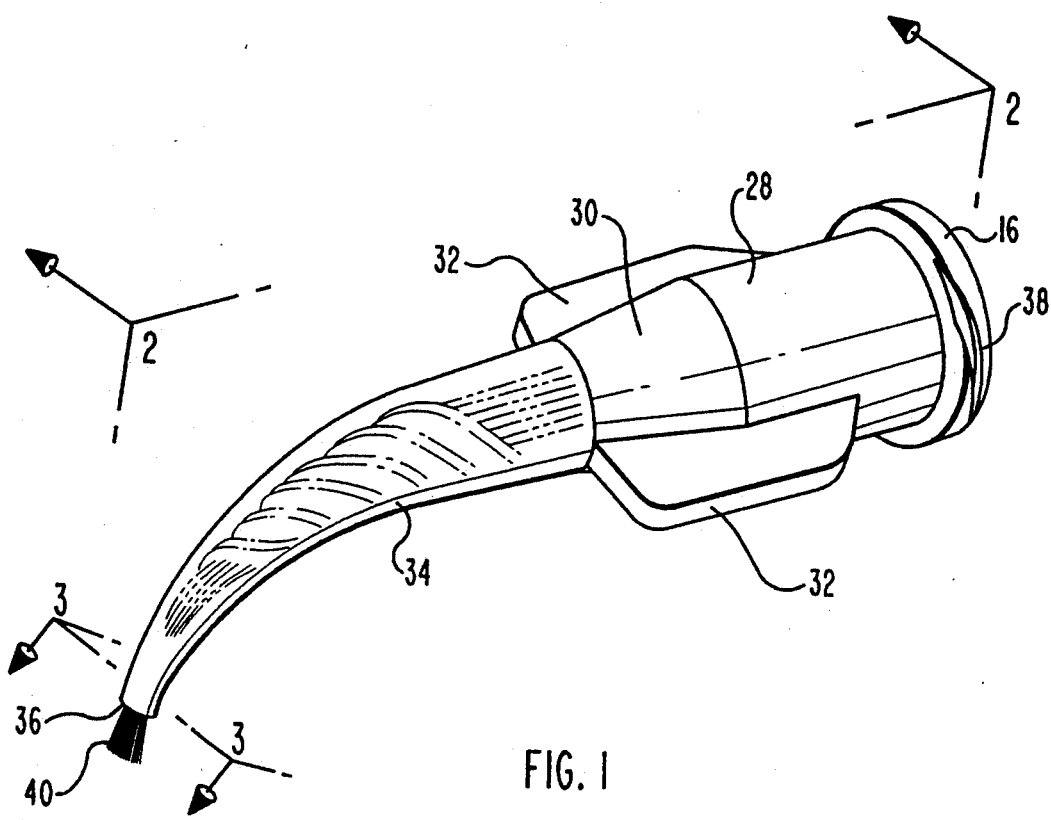
FIG. 1
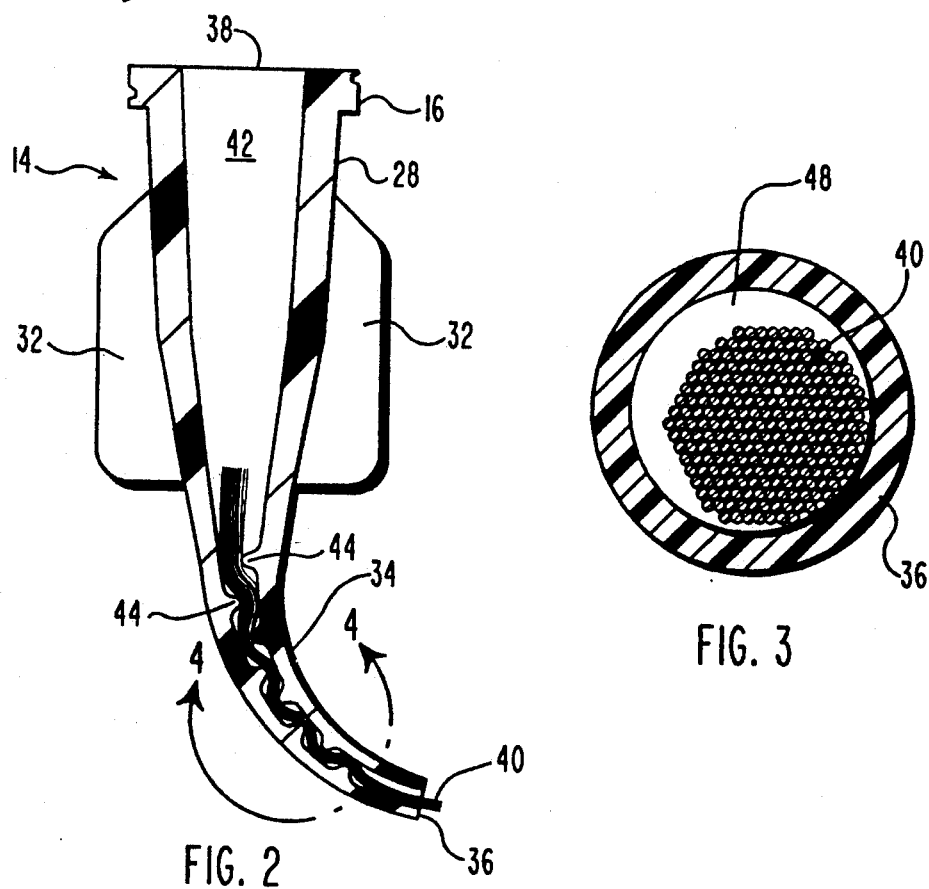
FIG. 2
FIG. 3

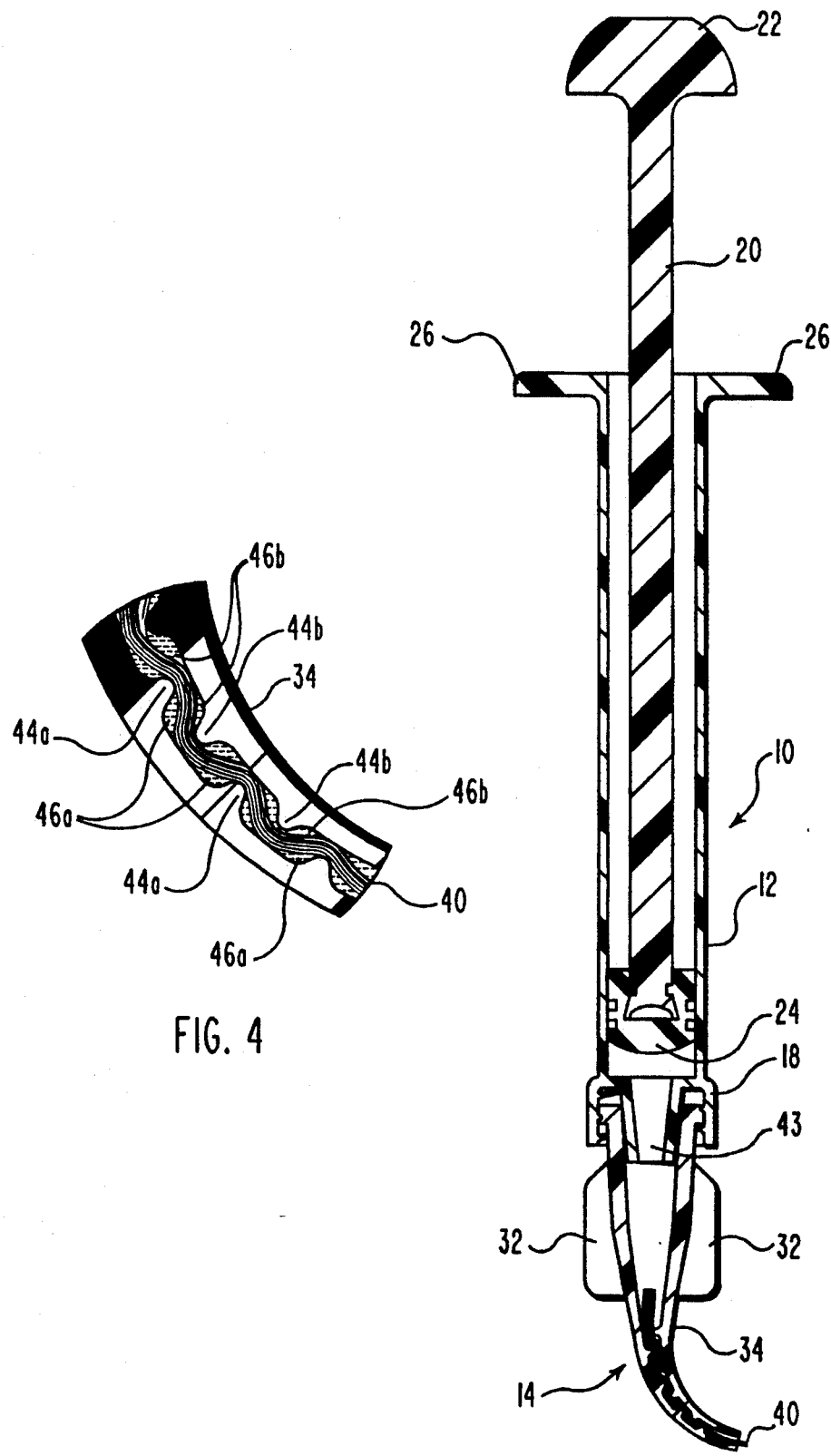

METHOD AND APPARATUS FOR DELIVERY OF HIGHLY FILLED, THIXOTROPIC SEALANT TO TEETH

This is a continuation-in-part of my copending application Ser. No. 07/940,204 filed Aug. 31, 1992, entitled "Adjustable Brush Delivery Tip With Secondary Flow Path."

BACKGROUND

1. The Field of the Invention

The present invention relates to methods and apparatus for delivering dental agents to tooth surfaces. More particularly, the present invention is ideally suited for applying a highly filled, thixotropic sealant to tooth surfaces in a manner which minimizes polymerization shrinkage and water absorption, and which provides for a stronger and more durable sealant so as to more effectively prevent tooth decay.

2. The Prior Art

Most dentists understand the value of using sealants as a prophylactic measure with emerging dentition. Sealants have proven to be an important adjunct to patient care. However, many clinicians avoid the usage of sealants due to products which fail to produce predictable, consistent results. This is due in significant measure to two factors. First, low-filled or unfilled resins have been the materials of choice to date, since low viscosity is necessary to maximize resin penetration into fissures. However, the problems with using low-filled or unfilled resins include shrinkage, increased water absorption, less strength, and less durability of the sealant.

On the other hand, to date, utilization of highly filled resin sealants e.g., those which contain approximately fifty percent (50%) filler has not been practical because the filler makes delivery using conventional delivery tips virtually impossible due to the high viscosity. For example, my prior U.S. Pat. No. 4,997,371, discloses a syringe-type dispenser with a removable applicator tip having bristles at the distal end thereof. The bristles are in communication with the syringe-type dispenser, thereby allowing a dental agent to be continuously applied to tooth surfaces without the need to stop the dental procedure and rewet the applicator. This device has proven to be highly effective with respect to the delivery of a number of different kinds of dental agents.

On the other hand, attempts to use this device for delivery of other dental agents that are more viscous or which are constituted of highly filled resins have proven unsatisfactory. For example, the bristles which are held by the applicator tip are primarily held by the frictional grip which occurs at the distal end of the tip. This causes the bristles to act as a filter, particularly with respect to any filler particles that are contained in the dental agent. Such filtering may change the physical properties of the dental agent as it is delivered to the tooth surface. For example, in the case of a bonding agent, filtering of the filler particles may make the actual bond weaker. Sometimes, such filtering can even tend to choke off the delivery tip, thus preventing flow of material. With some types of materials, such as highly filled sealants, it is virtually impossible to deliver the dental agent since the resistance to flow is simply too great and attempting to force the flow of the material through the applicator tip may actually cause the tip to be blown off, expelling undesired quantities of the material into the patient's mouth.

Accordingly, while it would be highly desirable to provide sealants which are highly filled (e.g., containing approximately fifty percent (50%) filler) so as to provide a sealant capable of greatly minimizing polymerization shrinkage and water absorption, while increasing strength and durability, to date there have not been adequate methods or apparatus available for accomplishing this result.

BRIEF SUMMARY AND OBJECTS OF THE INVENTION

The present invention seeks to resolve the above and other problems which have been experienced in the art. More particularly, the method and apparatus of this invention constitute an important advance in the art of dentistry, as evidenced by the following objects and advantages realized by the invention over the prior art.

The principal object of the present invention is to provide a method and apparatus for delivery of highly filled resin sealants to teeth, so as to provide a sealant and a method of applying the sealant which results in less polymerization shrinkage, less water absorption, greater strength and greater durability than have been heretofore available using prior art type sealants and methods of application for same.

The foregoing and other objects and advantages of the invention will be apparent from the description which follows, or may be learned by the practice of the invention. Briefly described, the present invention comprises a novel method and apparatus used for delivering to tooth surfaces a highly filled resin sealant. In the presently preferred embodiment of the invention, the resin sealant comprises a Bis-GMA resin sealant which contains approximately fifty percent (50%) filler, and which is a thixotropic agent. The apparatus of the present invention includes a dispenser such as a syringe, squeeze bulb or the like for holding the sealant and a delivery tip having bristles at one end. The delivery tip may be curved or straight and the bristles are slidably secured within the delivery tip by a helical ridge which is formed through a portion of a passageway that runs through the delivery tip. Spaces between the ridge form a tapered, spiral passageway or channel (hereinafter collectively referred to as a passageway) around the outside of the bristles. The spiral passageway enhances delivery of the thixotropic sealant by agitating the sealant as it flows through the spiral passageway around the bristles, thereby causing sheer thinning of the sealant as it is forced through the spiral passageway. Furthermore, space is provided at the distal end of the delivery tip where the bristles emerge to further enhance the ease of delivery. The novel delivery tip with its spiral passageway and bristles in combination with the thixotropic property of the sealant thus permit the highly filled resin sealant to be delivered to tooth surfaces with a high degree of precision. Further, once the sealant is delivered, it resists flowing on inclines because the sheer thinning action ends and the material becomes more viscous. The result is a sealant with the advantages of a composite and the penetration qualities of unfilled or low-filled sealant resin. This offers minimal shrinkage, improved wear resistance and greatly improved adhesion. The sealant may also be designed to release fluoride.

BRIEF DESCRIPTION OF THE DRAWINGS

In order to more fully understand the manner in which the above-recited advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the presently preferred embodiments and the presently understood best mode of the invention will be described with additional detail through use of the accompanying drawings in which:

FIG. 1 is a perspective view of the presently preferred embodiment of the syringe delivery tip of the present invention;

FIG. 2 is a longitudinal cross-sectional view of the embodiment of FIG. 1 taken along lines 2—2;

FIG. 3 is a cross-sectional view taken along lines 3—3 of the embodiment of FIG. 1 so as to particularly illustrate the manner in which the bristles do not occlude the distal end of the syringe delivery tip;

FIG. 4 is an enlarged cross-sectional view of the end of the syringe delivery tip taken along lines 4—4 of FIG. 2, so as to more particularly illustrate the manner in which the bristles are slidably secured by a helical ridge which forms a spiral passageway through the interior of the syringe delivery tip;

FIG. 5 is a longitudinal sectional view of the entire apparatus, including the syringe delivery tip as connected by a luer-lock coupling to a syringe apparatus which is used for controlling the delivery of a dental agent or coating through the delivery tip;

DETAILED DESCRIPTION OF THE PRESENTLY PREFERRED EMBODIMENT

1. The Apparatus

Figure 6:
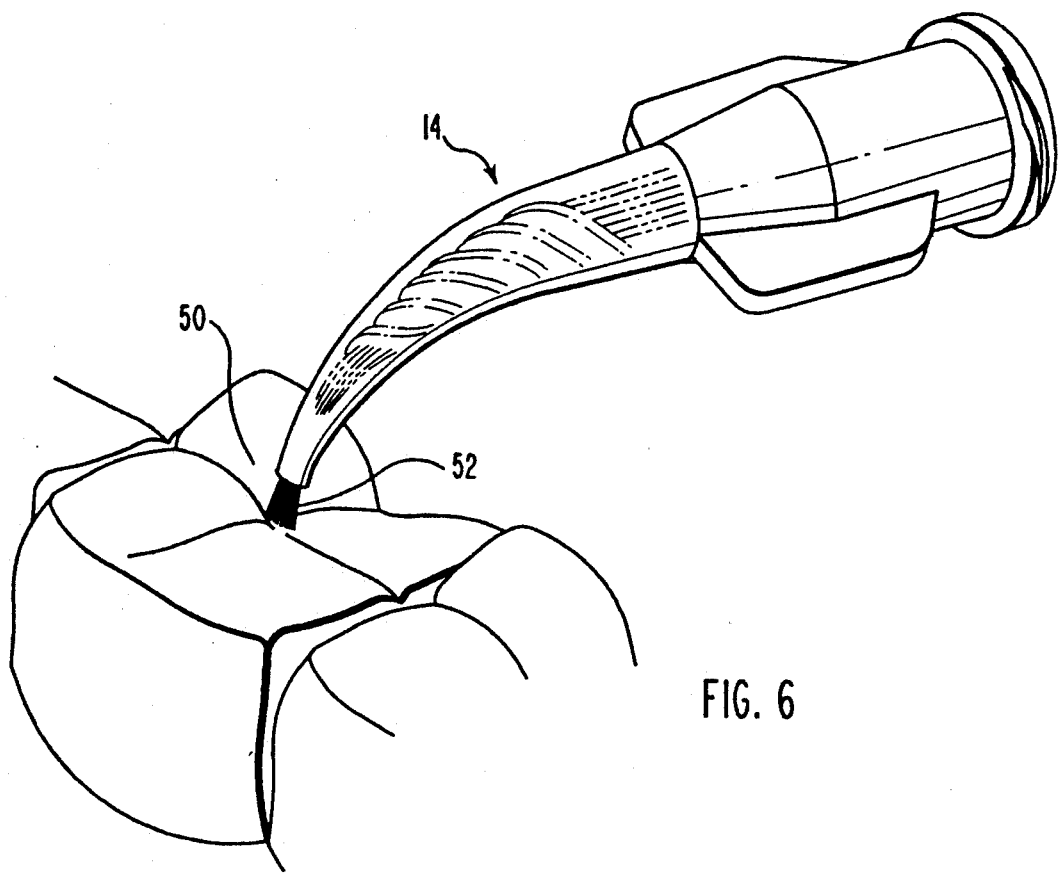
FIG. 6 is an enlarged perspective view which schematically illustrates one presently preferred mode of applying a dental agent or coating to a surface such as a tooth using a pin-point type delivery.

Reference is now made to the drawings wherein like parts are designated with like numerals throughout. Referring first to FIG. 5, one presently preferred embodiment of the apparatus of the present invention is illustrated and generally designated 10.

Applicator 10 includes a syringe barrel 12 and delivery tip 14. Syringe barrel 12 is generally cylindrical in shape and is adapted for holding a quantity of dental agent or other coating.

In the embodiment of the present invention illustrated in FIG. 5, delivery tip 14 is removable. Affixed to the lower end of syringe barrel 12 is a female luer-lock coupling 18. Removable delivery tip 14 is secured to syringe barrel 12 through coupling 18. Other means may be used to couple the delivery tip 14 to the syringe barrel 12. For example, a screw fit or press-fit coupling mechanism is suitable.

In another embodiment within the scope of the present invention, delivery tip 14 is permanently secured to the syringe barrel 12. The delivery tip 14 may be integrally molded as part of the syringe barrel 12 or it may snap on irreversibly to the syringe barrel 12. In such an embodiment, the syringe barrel 12 could be configured to hold only a sufficient quantity of dental agent or other coating for a single application. Thereafter, the device could be discarded.

Longitudinally slidable within syringe barrel 12 is plunger 20. Plunger 20 has at its proximal end a thumb disk 22 and at its distal end a plunger head 24. Plunger head 24 is constructed out of a resilient material such that its outer edge is contiguous with the inner wall of the syringe barrel 12. In addition, plunger head 24 is preferably constructed of a material which is non-reactive with the dental agent or coating.

At the proximal end of syringe barrel 12 is a pair of finger wings 26. Although conventional syringes function by placing two fingers on the finger wings 26 and depressing thumb disk 22 with the thumb, the present invention is preferably used by placing the fingers and thumb around the hand. This unique method of use gives the dentist or other user greater control in applying the dental agent or coating. Plunger 20 longitudinally enters syringe barrel 12. As a result, plunger head 24 presses against the dental agent or coating causing it to flow out of syringe barrel 12 and through the delivery tip 14.

The delivery tip 14 is more particularly illustrated with references to FIGS. 1-4, taken together. As shown best in FIG. 1, at the proximal end of the delivery tip 14, there is a male luer-lock threaded coupling 16 which is designed to mate with the corresponding female luer-lock coupling 18 of the syringe barrel 12. The delivery tip 28 has a cylindrical hub 28 which is tapered through conical section 30 and which joins to a nozzle 34, which may be curved as shown, or straight. Held within the curved nozzle 34 is a plurality of bristles 40, which as more particularly described hereinafter, can be used for application of the dental agent or coating using either a pin-point type application or a fanned out broad-brush type application. Also formed near the proximal end of the delivery tip 14 is a pair of fins 32 which are provided for convenience in threading the delivery tip 14 onto the syringe barrel 12.

As shown best in FIG. 2, the interior of the delivery tip 14 forms a passageway 42 which at its proximal end 38 is in communication with an outlet nozzle 43 (See FIG. 5) from which the dental agent or coating is discharged from the interior of the syringe barrel 12 into the passageway 42 of the delivery tip 14. Passageway 42 could take any desired cross-sectional shape, such as circular, elliptical, or even square, rectangular or polygonal. The passageway 42 is tapered from the proximal end 38 of the passageway 42 to the distal end 36.

Furthermore, as shown best in FIGS. 2 and 4 taken together, a helical ridge 44 is formed through a portion of the passageway 42. The spaces 46 between the ridge 44 form a spiral passageway in which the bristles 40 are slidably secured. Because the ridge 44 is formed as a helix through the interior of the passageway 42, as shown best in FIG. 4, on one side of the passageway 42 the helical ridges 44a project into the middle of the channels or spaces 46b formed between the ridges 44b on the other side of the passageway 42. Similarly, the helical ridges 44b on the other side of passageway 42 project into the middle of the spaces 44a in an alternating fashion. This causes the bristles 40 to be secured by the helical ridge 44 in a helical, undulating fashion as shown in FIGS. 2 and 4.

It has been found that by correctly dimensioning the ridge 44 in relation to the size and number of bristles 40 used in the brush, the brush slides when pushed or pulled, due to the friction by which the undulating bristles 40 are held by ridge 44. In a preferred embodiment, the ridge 44 is, for example, of from 0.004 to 0.005 inches high for the size bristles described below.

Importantly, the space 46 (see FIG. 4) which is left around the outside of the bristles 40 forms a tapered, spiral or helical passageway which enhances the delivery of the dental agent or coating when it is dispensed by means of pressing the plunger 20 into the syringe barrel 12. The spiral passageway 46 actually enhances the flow of the dental agent or coating around rather than through the bristles 40 and makes the delivery of the dental agent or coating much easier than if it were forced to flow through the bristles 40.

Particularly in the case of a thixotropic agent such as the highly filled resin sealant described below in connection with the method of the present invention, the spiral passageway provides a means for agitating the dental agent as it flows through the delivery tip thereby initiating sheer thinning of the agent. This advantageously temporarily lowers the viscosity of the thixotropic agent so as to provide effective delivery of the thixotropic agent through the delivery tip 14. Although the preferred embodiment has been illustrated using a single helical ridge 44, it is to be understood that any means of providing flow of the dental agent or coating around but not through the bristles is in keeping with the spirit and scope of the teaching of the present invention. For example, the spiral passageway could also be formed by forming two or more helical ridges opposing one another, such as two ridges 180° out of phase with one another. The passageway 46, though shown as a helical, spiraling passageway, could also take other forms. For example, a plurality of straight ridges might be used or the delivery tip could even have grooves formed in the interior wall of passageway 42 so as to form straight or spiral pathways through which the dental agent or coating could flow around, but not through, the bristles so as to enhance the ease of delivery.

As will be further appreciated particularly in reference to FIGS. 2 and 3, the ridge 44 preferably terminates prior to the distal end 36 of the delivery tip 14. The bristles 40 also do not need to be frictionally held by the distal end 36 of the delivery tip 14 as in the case of the prior art type device described above since they are held by ridge 44. Thus, there is a space 48 (See FIG. 3) at the distal end 36 of the delivery tip 14 through which the dental agent or coating is permitted to flow as it exits the delivery tip 14 and which also permits the dental agent or coating to be better dispersed among the bristles 40.

Because the dental agent or coating flows through the spiral, tapered passageway 46 around the bristles 40 rather than through the bristles 40, filler particles are not filtered out by the bristles 40 as in the case of the prior art type device and tip 14 is thus not clogged. Thus, substantially enhanced delivery of the dental agent or coating is accomplished by the delivery tip 14 of the present invention. For example, delivery of semiviscous or viscous material, which may or may not be viscous due to filler, may be virtually impossible to express using the prior art type delivery tip, but yet is easily expressed through the spiral passageway of the delivery tip of this invention.

In one currently preferred embodiment within the scope of the present invention, the bristle diameter is in the range from about 0.002 inches to about 0.005 inches, and preferably in the range from about 0.0025 inches to about 0.0035 inches. The bristles 40 typically extend beyond the distal end 36 of the delivery tip 14 a distance in the range from about 1/16 inch to about 5/16th inch. The bristles 40 typically extend into the passageway 42 of the delivery tip 14 a distance sufficient to fully engage the helical ridge 44 so that the helical ridge 44 will frictionally hold the bristles 40 but yet will permit the bristles 40 to be pulled out and lengthened if the user of the device so desires in order to permit either a pin-point type application or a fanned out, broad-brush type application, as described further below in reference to FIGS. 6 and 7. In one preferred embodiment with the scope of the present invention, the bristles extend into the passageway 42 of the delivery tip 14 in a range from about ¼ inch to about ½ inch.

The distance bristles 40 extend beyond the distal end 36 of delivery tip 14 may be manually adjusted by either pushing the bristles 40 further in or pulling them further out. Adjusting the length of the bristles 40 gives even greater control in applying the dental agent or coating. By pushing the bristles 40 further into delivery tip 14, the bristles are stiffer, which allows the dental agent to be worked more easily into surface irregularities such as pits and fissures, using more of a pin-point type control in applying the dental agent or coating. This is shown in conjunction with a tooth surface 50, using a pin-point type length 52 in FIG. 6. By pulling the bristles 40 further out from the delivery tip 14, the user can cause the bristles 40 to fan out and more easily coat a broader surface. This is shown in conjunction with a tooth surface 50a, using a longer length 54 in FIG. 7.

The syringe barrel 12, plunger 22, coupling 18, and delivery tip 14 are preferably constructed of rigid plastic, though other suitable construction materials such as glass or metal may be used. It is also important that the syringe barrel, plunger, coupling, and delivery tip be constructed of a material which will not react with the dental agent or coating used in the syringe. In addition, the dental agent or coating should not adhere to the construction material.

Because many dental agents or coatings are often light sensitive, the applicator 10 may be constructed of a light-resistive material. Thus, in that case the syringe barrel 12, delivery tip 14, plunger 20, and coupling 18 are preferably constructed of colored plastic that tends to filter out light. Different colored plastic may be used to identify the type of dental agent or coating within the syringe barrel. Alternatively, printing or other identifying markings on the syringe barrel may be used to identify the type of dental agent or coating. In addition, markings on the outer surface of the syringe barrel or plunger may be used to identify the volume of dental agent or coating used or remaining.

The plunger within the syringe barrel permits controlled dispensing of the dental agent or coating to the surface. It will be appreciated that other means may be used to control dispensing. For example, the applicator may be adapted for capsule use or for squeeze-bulb use.

2. The Method

One of the major limitations of many dental materials has been the necessity of mixing and applying them, with resultant mess and lack of control. Other materials and application methods do not require mixing, but interfere with patient care by proving cumbersome to use. Difficult delivery and uncertain results have caused frustration for many dentists in a variety of procedures; some dentists avoid certain procedures altogether due to a lack of confidence in an outcome favorable to both clinician and patient. As noted above, most dentists understand the value of using sealants as a prophylactic measure with emerging dentition. Sealants have proven to be an important adjunct to patient care. However, many clinicians avoid the use of sealants due to products which fail to produce predictable, consistent results. Low filled or unfilled resins have been the materials of choice to date, since low viscosity is necessary to maximize resin penetration into fissures. However, the use of low-filled or unfilled resins carries with it the disadvantage of greater polymerization shrinkage, increased water absorption, less strength, and faster wear than what has come to be expected from composites.

The above-described apparatus, in conjunction with the following described method largely solves the above problems. The method of this invention involves using a highly filled composite resin sealant so as to overcome the aforementioned problems of conventional sealants. In particular, the highly filled resin sealant used in conjunction with the method of the invention is comprised of a Bis-GMA resin sealant which contains approximately fifty percent (50%) sealer, and most preferably is the highly filled resin sealant sold under the trademark ULTRASEAL ® XT TM manufactured by Ultradent Products, Inc. of Salt Lake City, Utah. The highly filled resin sealant described is a thixotropic agent. The highly filled, thixotropic resin sealant is preloaded into a dispenser such as the syringe barrel 12 of the apparatus 10 (see FIG. 5). The syringe barrel is typically capped and stored until use. When ready for use, the cap is removed and the delivery tip 14 is attached to the syringe barrel in the manner heretofore described.

The occlusal surface of the tooth is first etched and then rinsed and dried after about 20 seconds. Suitable etching compounds are known in the art, one such compound being the product sold under the trademark ULTRA-ETCH ® manufactured by Ultradent Products, Inc. of Salt Lake City, Utah. Following the etching process, a hygroscopic drying and priming agent is then applied to the tooth surface. The drying and priming agent lifts any residual moisture from the fissures and primes the enamel to receive the sealant. A suitable drying and priming agent is the PRIMARY TM product manufactured by Ultradent Products, Inc. of Salt Lake City, Utah.

Figure 7:
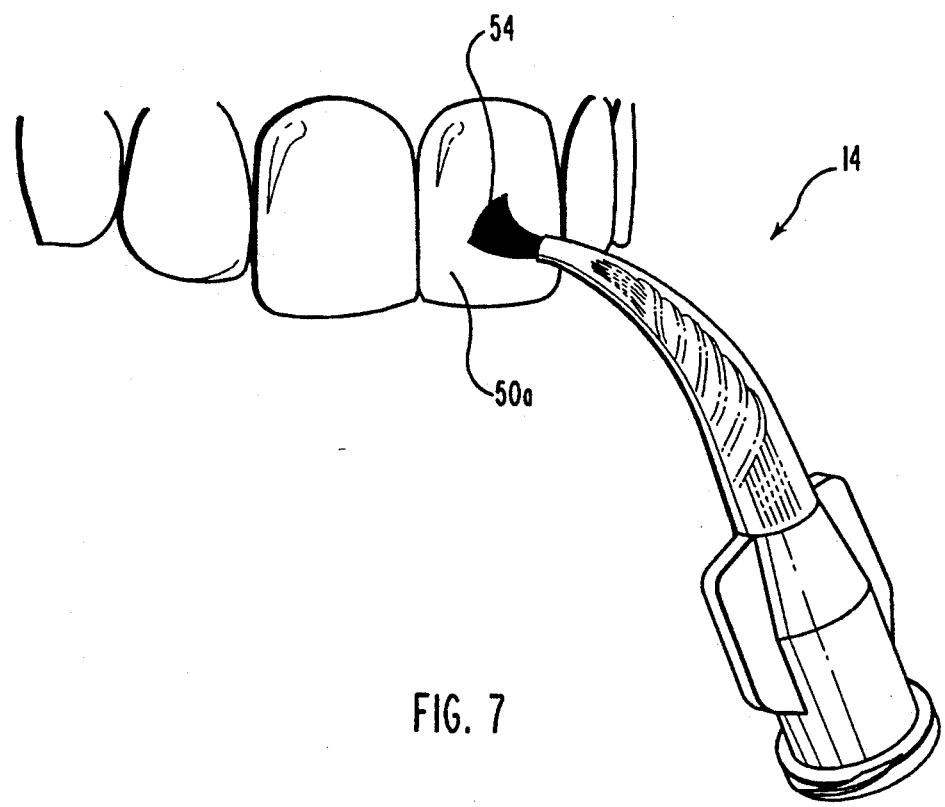
FIG. 7 is an enlarged perspective view which schematically illustrates a fanned out broad-brush type delivery of a dental agent or coating after the bristles have been extended in relation to the distal end of the syringe delivery tip.

After the drying and priming agent has been applied to the tooth surface, the apparatus 10 with the attached delivery tip 14 is then used to apply the highly filled resin sealant as described above. As shown, for example, in FIGS. 6 and 7, the bristles 40 may be shortened when applying the sealant to pits and fissures on the tooth surface using a pin-point length 52 which can be used with a scrubbing-type action to work the sealant into the pits and fissures on the tooth surface. The bristles can be lengthened as shown in FIG. 7 at reference numeral 54 when applying the sealant to broad, flat surfaces 50a on the tooth using a brush-like action.

Importantly, as the highly filled resin sealant is forced through the spiral passageway 46 around the outside of bristles 40 (see, e.g., FIGS. 2 and 4), the spiraling action which is imparted to the thixotropic sealant material causes sheer thinning. This, in conjunction with the fact that the sealant flows around but not through the bristles as it travels through the passageway 42 of the delivery tip 14, provides for unimpeded and effective delivery of the sealant to the distal end and out of the space 48 (see FIG. 3) at the distal end 36 of the delivery tip 14. As the sealant emerges, it is interspersed among the bristles 40 by capillary action and/or by working the bristles 40 back and forth.

In this manner, the highly filled resin sealant can be delivered directly to tooth surfaces without interrupting the procedure so as to apply an effective coating to the entire tooth surface. Furthermore, because of the thixotropic property of the resin sealant, once the sealant is delivered onto the tooth surface, it resists flowing on inclines because the sheer thinning action ends and the material becomes more viscous. The result is a sealant with the advantages of a composite and the penetration qualities of unfilled or low-filled resin sealant. The apparatus and method of the invention thereby provide for application of a highly filled resin sealant which minimizes shrinkage, improves wear resistance and provides superior adhesion, and when using the ULTRASEAL ® XT TM product described above also provides release of fluoride so as to provide highly effective action against tooth decay.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for delivery of a highly filled thixotropic resin sealant to a tooth surface, comprising the steps of:
    holding a quantity of the sealant in a reservoir means;
    delivering the sealant through a delivery tip to a brush comprising a plurality of bristles secured in a passageway of said tip, said step of delivering the sealant comprising the step of forcing the sealant through a secondary passageway that is located so as to cause the sealant to flow around but not through the bristles, and that is dimensioned and configured so as to cause sheer thinning of the sealant as it flows through the secondary passageway; and
    brushing the sealant onto the tooth surface using the bristles.

2. A method as defined in claim 1 wherein said step of forcing the sealant through the secondary passageway comprises the step of forcing the sealant through a tapered spiral passageway.

3. A method as defined in claim 2 wherein said reservoir means comprises a syringe barrel and a plunger, and said step of delivering the sealant further comprises the step of expelling the sealant from the syringe barrel by depressing the plunger so as to force the sealant into the delivery tip.

4. A method as defined in claims 2 or 3 wherein the tapered spiral passageway is defined by a helical ridge, and wherein said method further comprises the step of frictionally securing the bristles by means of the ridge.

5. A method as defined in claim 4 further comprising the step of selectively lengthening or shortening the bristles by either pulling them further out of the spiral passageway or by pushing them further into the spiral passageway.

6. A method as defined in claim 5 wherein said step of brushing the sealant comprises the step of applying the sealant to pits and fissures on the tooth surface using short bristles formed by pushing the bristles farther into the spiral passageway.

7. A method as defined in claim 5 wherein said step of brushing the sealant comprises the step of applying the sealant to broad, relatively flat tooth surfaces using longer bristles formed by pulling the bristles farther out of the spiral passageway.

* * * * *

UNITED STATES PATENT AND TRADEMARK OFFICE
CERTIFICATE OF CORRECTION

PATENT NO. : 5,246,371
DATED : September 21, 1993
INVENTOR(S) : DAN E. FISCHER

It is certified that error appears in the above-indentified patent and that said Letters Patent is hereby corrected as shown below:

```
Column 4, line 65, "spaces 44a" should be --spaces 46a--
Column 6, line 16, "with" should be --within--
Column 8, line 49, "PRIMARY" should be --PRIMADRY--
```

Signed and Sealed this

Twenty-third Day of August, 1994

Attest:

BRUCE LEHMAN

Attesting Officer

Commissioner of Patents and Trademarks